United States Patent
Dokania et al.

(10) Patent No.: US 11,064,600 B2
(45) Date of Patent: Jul. 13, 2021

(54) APPARATUS AND SYSTEM CONFIGURED TO CORRECT A CATHODE CURRENT AND A VOLTAGE BETWEEN A CATHODE AND AN ANODE FOR GENERATING X-RAYS

(71) Applicant: KONINKLIJKE PHILIPS N.V., Eindhoven (NL)

(72) Inventors: Anand Kumar Dokania, Utrecht (NL); Rolf Karl Otto Behling, Norderstedt (DE)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 0 days.

(21) Appl. No.: 16/612,783

(22) PCT Filed: May 30, 2018

(86) PCT No.: PCT/EP2018/064154
§ 371 (c)(1),
(2) Date: Nov. 12, 2019

(87) PCT Pub. No.: WO2018/224369
PCT Pub. Date: Dec. 13, 2018

(65) Prior Publication Data
US 2020/0154553 A1    May 14, 2020

(30) Foreign Application Priority Data
Jun. 8, 2017 (EP) .................................... 17174902

(51) Int. Cl.
*A61B 6/00* (2006.01)
*A61B 6/03* (2006.01)
(Continued)

(52) U.S. Cl.
CPC ............... *H05G 1/52* (2013.01); *A61B 6/032* (2013.01); *A61B 6/40* (2013.01); *A61B 6/405* (2013.01);
(Continued)

(58) Field of Classification Search
CPC .. H01J 35/06; H01J 35/10; H01J 35/14; H01J 35/147; H01J 35/153; H01J 35/08;
(Continued)

(56) References Cited

U.S. PATENT DOCUMENTS 4,827,494 A * 5/1989 Koenigsberg ........... H01J 35/14
378/137
4,979,199 A    12/1990 Cueman
(Continued)

FOREIGN PATENT DOCUMENTS

DE    19611228 C1    10/1997
JP    2002164197 A    6/2002
WO    WO2017060814 A1    4/2017

OTHER PUBLICATIONS

An English translation of DE19611228 C1 by Patent Translate dated May 25, 2020.*
(Continued)

*Primary Examiner* — Allen C. Ho
(74) *Attorney, Agent, or Firm* — Larry Liberchuk (57) ABSTRACT

At least one power supply produces a voltage between a cathode and an anode. The cathode and anode are operable such that electrons emitted from the cathode interact with the anode with energies corresponding to the voltage. The electrons interact with the anode at a focal spot to generate X-rays. The power supply provides the cathode with a cathode current. An electron detector is positioned relative to the anode, and a backscatter electron signal is measured from the anode. The measured backscatter electron signal is
(Continued)

provided to a processing unit, which determines a cathode current correction and/or a correction to the voltage between the cathode and the anode using the measured backscatter electron signal and a correlation between anode surface roughness and backscatter electron emission.

12 Claims, 5 Drawing Sheets

(51) Int. Cl.
| | |
|---|---|
| H01J 35/06 | (2006.01) |
| H01J 35/08 | (2006.01) |
| H01J 35/14 | (2006.01) |
| H05G 1/02 | (2006.01) |
| H05G 1/08 | (2006.01) |
| H05G 1/10 | (2006.01) |
| H05G 1/26 | (2006.01) |
| H05G 1/32 | (2006.01) |
| H05G 1/34 | (2006.01) |
| H05G 1/46 | (2006.01) |
| H05G 1/52 | (2006.01) |
| H05G 1/54 | (2006.01) |
| H01J 35/10 | (2006.01) |

(52) U.S. Cl.
CPC ............. *A61B 6/4021* (2013.01); *A61B 6/42* (2013.01); *A61B 6/4208* (2013.01); *A61B 6/4258* (2013.01); *A61B 6/44* (2013.01); *A61B 6/4429* (2013.01); *A61B 6/4435* (2013.01); *A61B 6/54* (2013.01); *A61B 6/542* (2013.01); *A61B 6/545* (2013.01); *A61B 6/58* (2013.01); *A61B 6/582* (2013.01); *H01J 35/06* (2013.01); *H01J 35/08* (2013.01); *H01J 35/10* (2013.01); *H01J 35/14* (2013.01); *H01J 35/147* (2019.05); *H01J 35/153* (2019.05); *H05G 1/02* (2013.01); *H05G 1/08* (2013.01); *H05G 1/10* (2013.01); *H05G 1/26* (2013.01); *H05G 1/265* (2013.01); *H05G 1/32* (2013.01); *H05G 1/46* (2013.01); *H05G 1/54* (2013.01)

(58) Field of Classification Search
CPC ........ H01J 35/112; H01J 35/116; H05G 1/02; H05G 1/08; H05G 1/10; H05G 1/26; H05G 1/265; H05G 1/32; H05G 1/34; H05G 1/46; H05G 1/52; H05G 1/54; H05G 1/30; A61B 6/032; A61B 6/40; A61B 6/4021; A61B 6/405; A61B 6/42; A61B 6/4208; A61B 6/4258; A61B 6/44; A61B 6/4429; A61B 6/4435; A61B 6/54; A61B 6/542; A61B 6/545; A61B 6/58; A61B 6/582
USPC .......... 378/16, 19, 98.6, 98.7, 108–113, 117, 378/118, 125, 137, 138, 144, 207
See application file for complete search history.

(56) References Cited

U.S. PATENT DOCUMENTS

| | | | | |
|---|---|---|---|---|
| 4,991,189 A * | 2/1991 | Boomgaarden | .......... | A61B 6/06 378/151 |
| 5,224,137 A * | 6/1993 | Plomgren | ............... | A61B 6/032 378/10 |
| 5,469,429 A * | 11/1995 | Yamazaki | ................ | H01J 35/24 378/113 |
| 5,550,886 A * | 8/1996 | Dobbs | .................... | A61B 6/032 378/19 |
| 5,583,903 A * | 12/1996 | Saito | ...................... | A61B 6/032 378/19 |
| 5,629,969 A * | 5/1997 | Koshishiba | .............. | G21K 7/00 378/138 |
| 5,633,906 A * | 5/1997 | Hell | ........................ | A61B 6/032 378/10 |
| 5,657,364 A * | 8/1997 | Pfoh | ....................... | A61B 6/035 378/137 |
| 5,745,548 A * | 4/1998 | Dobbs | ..................... | H05G 1/52 378/207 |
| 5,867,553 A * | 2/1999 | Gordon | .................. | A61B 6/032 378/4 |
| 6,094,469 A * | 7/2000 | Dobbs | .................. | A61B 6/4021 378/19 |
| 6,195,407 B1 * | 2/2001 | Dobbs | ................. | F16H 25/2409 378/19 |
| 6,252,935 B1 * | 6/2001 | Styrnol | .................... | H01J 35/10 378/137 |
| 6,256,364 B1 * | 7/2001 | Toth | .......................... | A61B 6/06 378/19 |
| 6,310,938 B1 * | 10/2001 | Toth | ....................... | A61B 6/583 378/147 |
| 6,322,248 B1 * | 11/2001 | Yanagita | ................. | A61B 6/032 378/11 |
| 6,333,968 B1 * | 12/2001 | Whitlock | ............... | B82Y 10/00 378/136 |
| 6,351,517 B1 | 2/2002 | Guru | | |
| 6,370,218 B1 * | 4/2002 | Toth | ....................... | A61B 6/032 378/113 |
| 6,385,279 B1 * | 5/2002 | Toth | ....................... | A61B 6/032 378/11 |
| 6,453,009 B2 * | 9/2002 | Berezowitz | .............. | H05G 1/26 378/118 |
| 6,542,576 B2 * | 4/2003 | Mattson | .................. | H01J 35/26 378/119 |
| 6,652,143 B2 * | 11/2003 | Popescu | ............ | G01N 23/046 378/207 |
| 7,050,542 B2 | 5/2006 | Bathe | | |
| 7,233,645 B2 * | 6/2007 | Feda | .................... | G01N 23/223 378/102 |
| 7,266,179 B2 * | 9/2007 | Deuringer | ............... | H01J 35/14 378/137 |
| 7,284,905 B2 * | 10/2007 | Kühn | ..................... | A61B 6/032 378/119 |
| 7,286,639 B2 * | 10/2007 | Shen | ...................... | A61B 6/032 250/370.09 |
| 7,302,041 B2 | 11/2007 | Deuringer | | |
| 7,654,740 B2 * | 2/2010 | Behling | ................... | H01J 35/10 378/125 |
| 8,654,924 B2 | 2/2014 | Behling | | |
| 8,761,342 B2 * | 6/2014 | Behling | ................... | H01J 35/10 378/137 |
| 8,934,006 B2 * | 1/2015 | Chino | ..................... | H01J 37/26 348/80 |
| 8,958,530 B2 | 2/2015 | Behling | | |
| 9,370,084 B2 * | 6/2016 | Sprang | ..................... | H05G 1/30 |
| 9,480,444 B2 * | 11/2016 | Kappler | ................... | A61B 6/032 |
| 9,538,979 B2 * | 1/2017 | Behling | .................. | H01J 35/18 |
| 9,594,036 B2 * | 3/2017 | Yun | ..................... | G01N 23/2076 |
| 9,767,986 B2 * | 9/2017 | Brown | ................... | G01N 30/72 |
| 9,934,930 B2 * | 4/2018 | Parker | ................... | H01J 35/112 |
| 9,984,847 B2 * | 5/2018 | Shirota | .................. | G01N 23/04 |
| 10,283,313 B2 * | 5/2019 | Nonoguchi | ........... | H01J 35/147 |
| 10,757,795 B2 * | 8/2020 | Miller | ..................... | A61B 6/032 |
| 10,784,069 B2 * | 9/2020 | Tuohimaa | ................ | H05G 1/52 |
| 2001/0031036 A1 | 10/2001 | Berezowitz | | |
| 2004/0247080 A1 | 12/2004 | Feda | | |
| 2005/0100133 A1 | 5/2005 | Reinhold | | |
| 2007/0189463 A1 | 8/2007 | Deuringer | | |
| 2009/0067578 A1 | 3/2009 | Behling | | |
| 2010/0020938 A1 | 1/2010 | Koch | | |
| 2011/0235784 A1 | 9/2011 | Behling | | |
| 2013/0083901 A1 | 4/2013 | Grasruck | | |
| 2013/0223594 A1 | 8/2013 | Sprong | | |
| 2014/0177810 A1 | 6/2014 | Gao | | |
| 2015/0006093 A1 | 1/2015 | Hess | | |

(56) References Cited

U.S. PATENT DOCUMENTS

2016/0064184 A1   3/2016  Brown
2016/0178540 A1   6/2016  Yun
2016/0183907 A1   6/2016  Behling

OTHER PUBLICATIONS

An English translation of DE 196 11 228 C1 by Patent Translate.*
PCT International Search Report, International application No. PCT/EP2018/064154, dated Jul. 2, 2018.
Kenji Nishimura et al: "Influence of Surface Roughness on Secondary Electron Emission and Electron Backscattering from Metal Surface", Japanese Journal 0f Applied Physics, vol. 33, No. Part 1, No. 8, Aug. 15, 1994 (Aug. 15, 1994), pp. 4727-4734, XP055429349.
R. Behling. 2016. Modern Diagnostic X-Ray Sources: Technology, Manufacturing, Reliability. CRC Press, Taylor & Francis, Boca Raton, USA, 2016.
IS/IEC 60336, 2005: "Medical Electrical Equipment—X-Ray Tube Assemblies for Medical Diagnosis—Characteristics of Focal Spots", International Electrotechniical Commission (IEC), Ed. 4. Geneva, Switzerland: International Electrotechnical Commission.
Mehranian A. et al., "Quantitative Assessment of the Effect of Anode Surface Roughness on Diagnostic X-ray Spectra: A Monte Carlo Simulation Study", 2009 IEEE Nuclear Science Symposium Conference Record M05-361, pp. 2902-2907.
Erdelyi M. et al., "Measurement of the X-Ray Tube Anodes' Surface Profile and its Effects on the X-Ray Spectra", Medical Physics, vol. 36, Issue 2, 2009, pp. 587-593.
Kakonyi R. et al., "Monte Carlo Simulation of the Effects of Anode Surface Roughness on X-Ray Spectra", Medical Physics, vol. 37, Issue 11, 2010, pp. 5737-5745.

\* cited by examiner

APPARATUS AND SYSTEM CONFIGURED TO CORRECT A CATHODE CURRENT AND A VOLTAGE BETWEEN A CATHODE AND AN ANODE FOR GENERATING X-RAYS

FIELD OF THE INVENTION

The present invention relates to an apparatus for generating X-rays, to a system for imaging an object, to a method for generating X-rays, as well as to a computer program element and a computer readable medium. The invention also relates to an apparatus and method for controlling a focused electron beam used in generating X-rays.

BACKGROUND OF THE INVENTION

The general background of this invention is the generation of X-rays. Anode target deterioration is one of the causes of tube aging especially for Computer Tomography (CT) tubes, leading to decrease in X-ray flux with tube aging. It is well known that the X-ray output of a tube decreases with usage due to roughening of the surface of the X-ray emitting area of the anode target, which causes self-filtration. The considerable effect of surface roughness and cracks on the reduction of x-ray output spectra (5-20% reduction in flux) is reported for example in: M. Erdélyi et al, Measurement of the x-ray tube anodes' surface profile and its effects on the x-ray spectra, Medical Physics, Vol. 36, Issue 2, 2009, pp. 587-593; R. Kákonyi et al, Monte Carlo simulation of the effects of anode surface roughness on x-ray spectra, Medical Physics, Vol. 37, Issue 11, 2010, pp. 5737-5745; and A. Mehranian et al, Quantitative Assessment of the Effect of Anode Surface Roughness on the Diagnostic X-ray Spectra Using Monte Carlo Simulation, 2009 IEEE Nuclear Science Symposium Conference Record M05-361, pp. 2902. Methods to extract information on anode aging based on X-ray flux or dose drop calibration have been described in US2013/0083901A1, US2014/0177810A1, and US2007/0189463A1. Furthermore, the location and size of the focal spot of the electron beam on the rotating anode fluctuates. The location can fluctuate due to anode wobble, centrifugal forces, gravitational, mechanical instabilities of the cathode and/or anode fastening or the mounting in the x-ray system. The size can fluctuate due to electronic space charge, mechanical instabilities such as movement of the electron emitter, change of the magnetic or electric focusing fields. Normally, such fluctuations are mitigated by implementing extra margins such as the focal spot being designed to be smaller than required to ensure that even under the worst case conditions the focal spot size and location is as required. Therefore in light of such issues, to maintain maximum X-ray flux, the power delivered the anode must be increased thereby exacerbating deterioration of the anode, or increase mechanical friction loss in hydrodynamic bearings due to a required increase in rotational speed of the anode. Alternatively, a reduction in maximum X-ray flux must be accepted.

SUMMARY OF THE INVENTION

It would be advantageous to have improved apparatus for generating X-rays.

The object of the present invention is solved with the subject matter of the independent claims, wherein further embodiments are incorporated in the dependent claims. It should be noted that the following described aspects and examples of the invention apply also for the apparatus for generating X-rays, the system for imaging an object, the method for generating X-rays, the apparatus for controlling a focused electron beam, method for controlling a focused electron beam, and for the computer program element and the computer readable medium.

According to a first aspect, there is provided an apparatus for generating X-rays, comprising:

a cathode;
an anode;
at least one power supply;
an electron detector; and
a processing unit.

The at least one power supply is configured to produce a voltage between the cathode and the anode. The at least one power supply is also configured to provide the cathode with a cathode current. The cathode is positioned relative to the anode, and the cathode and anode are operable such that electrons emitted from the cathode interact with the anode with energies corresponding to the voltage. The electrons interact with the anode at a focal spot to generate X-rays. The electron detector is positioned relative to the anode, and is configured to measure a backscatter electron signal from the anode. The electron detector is configured to provide the measured backscatter electron signal to the processing unit. The processing unit is configured to determine a cathode current correction and/or a correction to the voltage between the cathode and the anode. The determination comprises utilization of the measured backscatter electron signal and a correlation between anode surface roughness and backscatter electron emission. The processing unit is configured to provide the cathode current correction and/or the correction to the voltage between the cathode and the anode to the at least one power supply.

In other words, it is known that X-ray emission changes with surface roughness of an anode, where the surface of an anode deteriorates through use, and using a correlation between surface anode roughness and backscatter electron emission an appropriate adjustment of the X-ray tube current can be made in order to maintain the X-ray emission at an optimum level on the basis of a measured backscatter electron signal. This means not only can the apparatus auto-correct the X-ray flux through appropriate correction of the X-ray tube current and/or a correction to the voltage between the cathode and the anode, remedial work by field service engineers does not have to be initiated as frequently, thereby saving costs.

Constant monitoring can help predict remaining lifetime of tube thus help in predictive maintenance, system uptime and better service contracts.

In an example, the determination comprises utilization of a correlation between anode surface roughness and X-ray emission.

Thus having a correlation between backscatter electron emission and surface roughness a measured backscatter electron signal can be used to determine a surface roughness of the anode. Then on the basis of a correlation between anode surface roughness and X-ray emission, the change in X-ray emission that will have occurred due to a change in surface roughness can be determined (from the measured backscatter electron signal) and the cathode current (X-ray tube current) and/or the voltage between the cathode and the anode can be appropriately adjusted to, for example, maintain the X-ray emission at the same level.

In an example, the backscatter electron signal comprises a backscatter electron current.

In an example, the electron detector comprises a plurality of electron detecting elements and an aperture, and wherein the aperture is positioned between the anode and the plurality of electron detecting elements.

In other words, an X-ray pinhole camera is used to determine characteristics of the electron beam focused on the anode on the basis of direct electron detection. Thus high signals are obtainable, with high spatial resolution and dynamic range. Knowing the characteristics of the electron focal spot appropriate feed-back loops maintaining that focal spot in an optimum form can then be implemented.

In an example, the processing unit is configured to determine a size of the focal spot, wherein the determination utilizes the measured backscatter electron signal.

In an example, the processing unit is configured to determine a location of the focal spot, wherein the determination utilizes the measured backscatter electron signal.

In an example, the at least one power supply is configured to provide at least one voltage to focus the electrons at the focal spot; and wherein the processing unit is configured to determine a correction to the at least one voltage to focus the electrons at the focal spot; and wherein the processing unit is configured to provide the correction to the at least one power supply.

In this way, because the location and size of the electron focal spot can be held at the correct position, the size of the electron beam focal spot can be maximized for a particular application. This means that X-ray fluxes can be maximized for a particular electron power density on the anode, because the focal spot does not need to be smaller than the optimum due to beam wander and focal spot size variation.

In an example, the backscatter electron signal comprises a backscatter electron flux.

In an example, the electron detector is configured to measure an X-ray flux from the anode.

In other words, the electron detector is also a photon detector. Thus by measuring the backscatter electron flux and X-ray flux from the anode at the same time, the X-ray tube voltage can be determined because the ration of electron to photon flux depends on the acceleration voltage. In this way, not only can the cathode current be corrected within an auto-correction process but a check can be made, on the basis of electron and photon fluxes, that the X-ray tube is operating at the correct voltage.

In an example, the electron detector comprises a scintillator.

According to a second aspect, there is provided an apparatus for controlling a focused electron beam, comprising:
a cathode;
an anode;
at least one power supply;
an electron detector; and
a processing unit.

The cathode is positioned relative to the anode, and the cathode and anode are operable such that electrons emitted from the cathode interact with the anode at a focal spot to generate X-rays. The at least one power supply is configured to provide at least one voltage to focus the electrons at the focal spot. The electron detector is positioned relative to the anode, and is configured to measure a backscatter electron signal from the anode. The electron detector comprises a plurality of electron detecting elements and an aperture. The aperture is positioned between the anode and the plurality of electron detecting elements. The electron detector is configured to provide the measured backscatter electron signal to the processing unit. The processing unit is configured to determine a size of the focal spot and/or a location of the focal spot. The determination utilizes the measured backscatter electron signal. The processing unit is also configured to determine a correction to the at least one voltage to focus the electrons at the focal spot. The processing unit is configured to provide the correction to the at least one power supply.

In this manner, because the size and/or location the electron focal spot can determined a correction can be made to maximize the size of the focused electron beam and/or more correctly locate the focused electron beam. This means that X-ray fluxes can be maximized for a particular electron power density on the anode, because the focal spot does not need to be smaller than the optimum due to beam wander and/or focal spot size variation. Furthermore, for a required X-ray flux the electron power density can be reduced providing for longevity of the anode, and/or gantry rotational rates can be reduced leading to a reduction in mechanical friction loss in hydrodynamic bearings.

According to a third aspect, there is provided a system for imaging an object, comprising:
an apparatus for generating X-rays according to the first aspect;
an X-ray detector; and
an output unit.

The cathode and the anode are configured to be positioned relative to the X-ray detector such that at least a part of the region between them is an examination region for accommodating an object. The X-ray detector is configured to acquire image data of the object. The output unit is configured to output data representative of the image data of the object.

In this way, the cathode and the anode are positioned such that between the cathode/anode and the X-ray detector there is provided an examination region for accommodating an object.

According to a fourth aspect, there is provided a method for generating X-rays, comprising:
(a) producing with at least one power supply a voltage between a cathode and an anode, wherein, the cathode is positioned relative to the anode, and the cathode and anode are operable such that electrons emitted from the cathode interact with the anode with energies corresponding to the voltage, and wherein the electrons interact with the anode at a focal spot to generate X-rays;
(b) providing with the at least one power supplies the cathode with a cathode current;
(c) positioning an electron detector relative to the anode, and measuring a backscatter electron signal from the anode;
(d) providing the measured backscatter electron signal to a processing unit;
(e) determining with the processing unit a cathode current correction and/or a correction to the voltage between the cathode and the anode, wherein the determination comprises utilization of the measured backscatter electron signal and a correlation between anode surface roughness and backscatter electron emission; and
(h) providing the cathode current correction and/or the correction to the voltage between the cathode and the anode to the at least one power supply.

According to a fifth aspect, there is provided method for controlling a focused electron beam, comprising:
(a1) positioning a cathode relative to an anode, and the cathode and anode are operable such that electrons emitted from the cathode interact with the anode at a focal spot to generate X-rays;
(b1) providing with at least one power supply at least one voltage to focus the electrons at the focal spot;
(c1) positioning an electron detector relative to the anode, wherein the electron detector is configured to measure a backscatter electron signal from the anode, and wherein the electron detector comprises a plurality of electron detecting elements and an aperture, and wherein the aperture is positioned between the anode and the plurality of electron detecting elements;

(d1) providing the measured backscatter electron signal to a processing unit;

(e1) determining by the processing unit a size of the focal spot and/or a location of the focal spot, wherein the determination utilizes the measured backscatter electron signal; and (f1) determining with the processing unit a correction to the at least one voltage to focus the electrons at the focal spot; and wherein the processing unit is configured to provide the correction to the at least one power supply.

According to another aspect, there is provided a computer program element controlling apparatus as previously described which, if the computer program element is executed by a processing unit, is adapted to perform the method steps as previously described.

According to another aspect, there is provided a computer readable medium having stored computer element as previously described.

Advantageously, the benefits provided by any of the above aspects equally apply to all of the other aspects and vice versa.

The above aspects and examples will become apparent from and be elucidated with reference to the embodiments described hereinafter.

BRIEF DESCRIPTION OF THE DRAWINGS

Exemplary embodiments will be described in the following with reference to the following drawings.

DETAILED DESCRIPTION OF EMBODIMENTS

Figure 1:
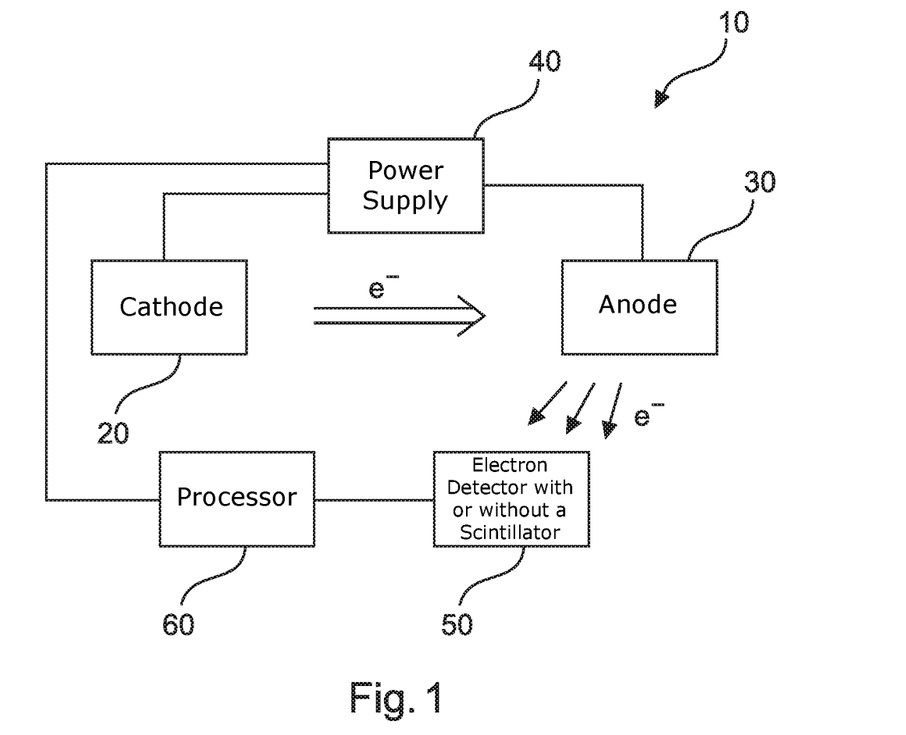
FIG. 1 shows a schematic set up of an example of an apparatus for generating X-rays.

FIG. 1 shows an example of an apparatus 10 for generating X-rays. The apparatus 10 comprises a cathode 20, an anode 30, at least one power supply 40, an electron detector 50 and a processing unit 60. The at least one power supply 40 is configured to produce a voltage between the cathode 20 and the anode 30. The at least one power supply 40 is configured to provide the cathode 20 with a cathode current. The cathode 20 is positioned relative to the anode 30, and the cathode 20 and anode 30 are operable such that electrons emitted from the cathode 20 interact with the anode 30 with energies corresponding to the voltage. The electrons interact with the anode 30 at a focal spot to generate X-rays. The electron detector 50 is positioned relative to the anode 30, and is configured to measure a backscatter electron signal from the anode 30. The electron detector 50 is configured to provide the measured backscatter electron signal to the processing unit 60. This is via a wired or wireless communication. The processing unit 60 is configured to determine a cathode current correction. The determination comprises utilization of the measured backscatter electron signal and a correlation between anode surface roughness and backscatter electron emission. The processing unit 60 is configured to provide the cathode current correction to the at least one power supply 40. This is via a wired or wireless communication.

In an example, the processing unit 60 is configured to determine a correction to the voltage between the cathode 20 and anode 30, wherein the determination comprises utilization of the measured backscatter electron signal and a correlation between anode surface roughness and backscatter electron emission, and the processing unit 60 is configured to provide the voltage correction to the at least one power supply 40. In this way, cathode current and X-ray tube voltage corrections can be determined and provided in order to keep the generation of X-rays at an optimum level.

According to an example, the determination comprises utilization of a correlation between anode surface roughness and X-ray emission.

According to an example, the backscatter electron signal comprises a backscatter electron current.

According to an example, the electron detector 50 comprises a plurality of electron detecting elements and an aperture, and wherein the aperture is positioned between the anode 30 and the plurality of electron detecting elements.

In an example, the measured backscatter electron signal, when processed by the processing unit 60, comprises a point (line) spread function.

According to an example, the processing unit 60 is configured to determine a size of the focal spot, wherein the determination utilizes the measured backscatter electron signal.

According to an example, the processing unit 60 is configured to determine a location of the focal spot, wherein the determination utilizes the measured backscatter electron signal.

According to an example, the at least one power supply 40 is configured to provide at least one voltage to focus the electrons at the focal spot. The processing unit 60 is configured to determine a correction to the at least one voltage to focus the electrons at the focal spot, and the processing unit 60 is configured to provide the correction to the at least one power supply 40. This is via a wired or wireless communication.

According to an example, the backscatter electron signal comprises a backscatter electron flux.

According to an example, the electron detector 50 is configured to measure an X-ray flux from the anode 30.

According to an example, the electron detector 50 comprises a scintillator. With continued reference to FIG. 1, the electron detector 50 can be used in a self-contained apparatus 10 for controlling the focused electron beam. In this apparatus 10 for controlling a focused electron beam, there is a cathode 20, an anode 30, at least one power supply 40. The at least one power supply 40 does not need to provide a voltage between the cathode 20 and anode 30 or provide a cathode current, but it can do can and thus in an example the at least one power supply 40 has the same capabilities as the at least one power supply 40. The apparatus 10 for controlling the focused electron beam also comprises an electron detector 50 and a processing unit 60. The cathode 20 is positioned relative to the anode 30, and the cathode 20 and anode 30 are operable such that electrons emitted from the cathode 20 interact with the anode 30 at a focal spot to generate X-rays. The at least one power supply 40 is configured to provide at least one voltage to focus the electrons at the focal spot. The electron detector 50 is positioned relative to the anode 30, and is configured to measure a backscatter electron signal from the anode 30. The electron detector 50 comprises a plurality of electron detecting elements and an aperture. The aperture is positioned between the anode 30 and the plurality of electron detecting elements. The electron detector 50 is configured to provide the measured backscatter electron signal to the processing unit 60 via a wired or wireless communication. The processing unit 60 is configured to determine a size of the focal spot and/or a location of the focal spot. The determination utilizes the measured backscatter electron signal. The processing unit 60 is also configured to determine a correction to the at least one voltage to focus the electrons at the focal spot. The processing unit 60 is configured to provide the correction to the at least one power supply 40.

Figure 2:
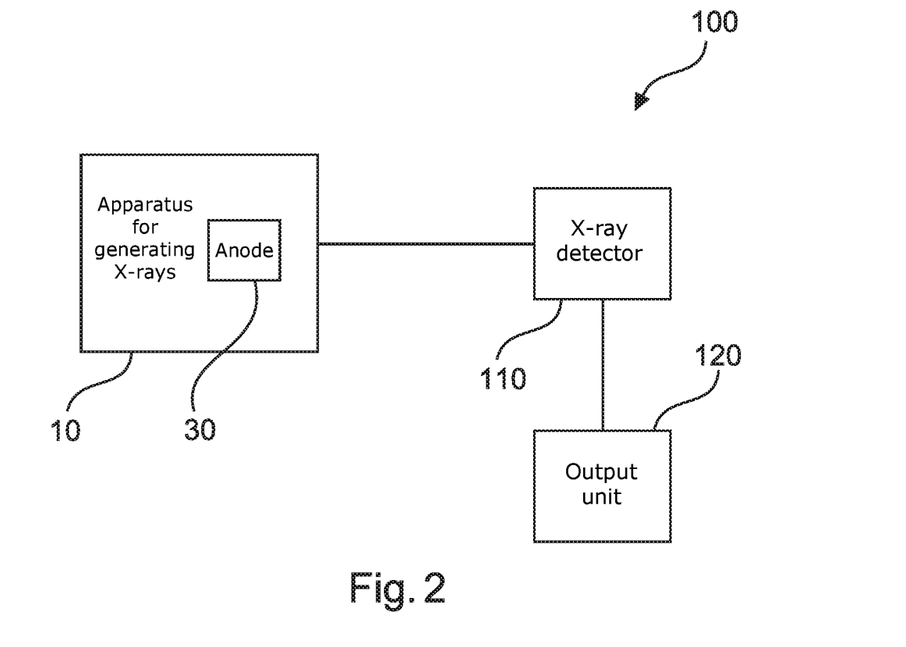
FIG. 2 shows a schematic set up of an example of a system for imaging an object.

FIG. 2 shows as example of a system 100 for imaging an object. The system 100 comprises an apparatus 10 for generating X-rays as described in any of the examples with reference to FIG. 1. The system 100 also comprises an X-ray detector 110 and an output unit 120. The cathode 20 and the anode 30 are configured to be positioned relative to the X-ray detector 110 such that at least a part of the region between them is an examination region for accommodating an object. The X-ray detector 110 is configured to acquire image data of the object. The output unit 120 is configured to output data representative of the image data of the object.

Figure 3:
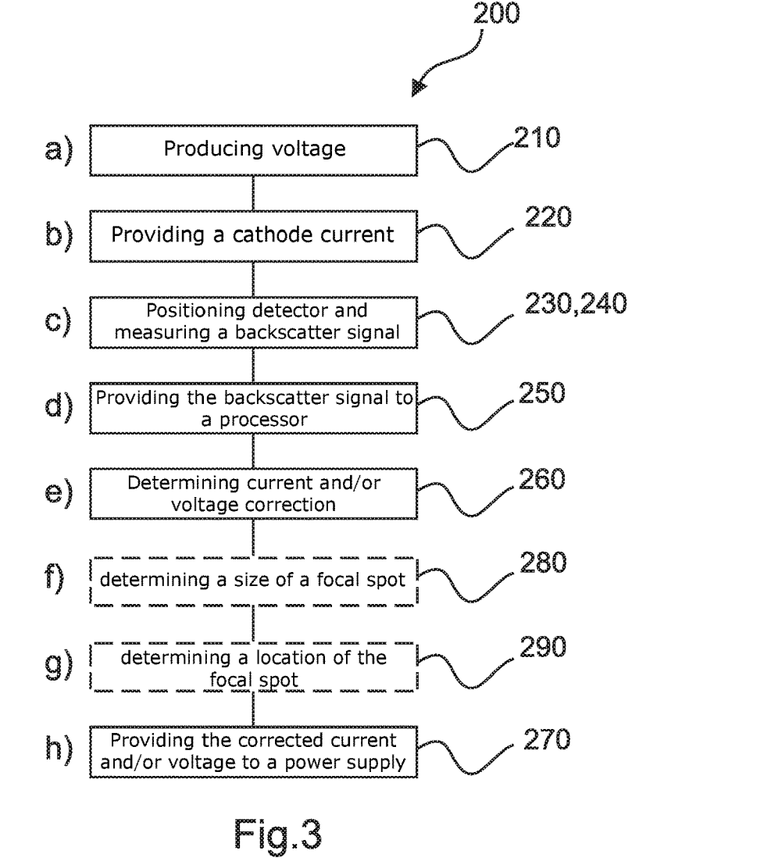
FIG. 3 shows a method for generating X-rays.

FIG. 3 shows a method 200 for generating X-rays in its basic steps. The method 200 comprises:

in a producing step 210, also referred to as step (a), producing with at least one power supply 40 a voltage between a cathode 20 and an anode 30, wherein, the cathode 20 is positioned relative to the anode 30, and the cathode 20 and anode 30 are operable such that electrons emitted from the cathode 20 interact with the anode 30 with energies corresponding to the voltage, and wherein the electrons interact with the anode 30 at a focal spot to generate X-rays;

in a providing step 220, also referred to as step (b), providing with the at least one power supply 40 the cathode 20 with a cathode current;

in a positioning 230 and measuring step 240, also referred to as step (c), positioning an electron detector 50 relative to the anode 30, and measuring a backscatter electron signal from the anode 30;

in a providing step 250, also referred to as step (d), providing the measured backscatter electron signal to a processing unit 60;

in a determining step 260, also referred to as step (e), determining with the processing unit 60 a cathode current correction and/or a correction to the voltage between the cathode 20 and the anode 30, wherein the determination comprises utilization of the measured backscatter electron signal and a correlation between anode surface roughness and backscatter electron emission; and in a providing step 270, also referred to as step (h), providing the cathode current correction and/or the correction to the voltage between the cathode 20 and the anode 30 to the at least one power supply 40.

In an example, step (e) comprises utilizing a correlation between anode surface roughness and X-ray emission.

In an example, the backscatter electron signal comprises a backscatter electron current.

In an example, the electron detector 50 comprises a plurality of electron detecting elements and an aperture, and wherein the aperture is positioned between the anode 30 and the plurality of electron detecting elements.

In an example, the method comprises step f) determining 280 a size of the focal spot, wherein the determination utilizes the measured backscatter electron signal.

In an example, the method comprises step g) determining 290 a location of the focal spot, wherein the determination utilizes the measured backscatter electron signal.

In an example, the at least one power supply 40 is configured to provide at least one voltage to focus the electrons at the focal spot; and wherein the method comprises determining with the processing unit 60 a correction to the at least one voltage to focus the electrons at the focal spot; and providing the correction to the at least one voltage to focus the electrons at the focal spot to the at least one power supply 40.

In an example, the backscatter electron signal comprises a backscatter electron flux.

In an example, method comprises measuring with the electron detector 50 an X-ray flux from the anode 30.

In an example, the electron detector 50 comprises a scintillator.

In an example, that is not shown in an associated figure but is clearly described here, there is provided a method for controlling a focused electron beam, comprising:

in a positioning step, positioning a cathode 20 relative to an anode 30, and the cathode 20 and anode 30 are operable such that electrons emitted from the cathode 20 interact with the anode 30 at a focal spot to generate X-rays;

in a providing step, providing with at least one power supply 40 at least one voltage to focus the electrons at the focal spot;

in a positioning step, positioning an electron detector 50 relative to the anode 30, wherein the electron detector 50 is configured to measure a backscatter electron signal from the anode 30, and wherein the electron detector 50 comprises a plurality of electron detecting elements and an aperture, and wherein the aperture is positioned between the anode 30 and the plurality of electron detecting elements;

in a providing step, providing the measured backscatter electron signal to a processing unit 60;

in a determining step, determining by the processing unit 60 a size of the focal spot and/or a location of the focal spot, wherein the determination utilizes the measured backscatter electron signal; and in a determining step, determining with the processing unit 60 a correction to the at least one voltage to focus the electrons at the focal spot; and wherein the processing unit 60 is configured to provide the correction to the at least one power supply 40.

The apparatus 10 for generating X-rays, system 100 for imaging an object, and method for generating X-rays are now described in more detail in conjunction with FIGS. 4-9.

Figure 4:
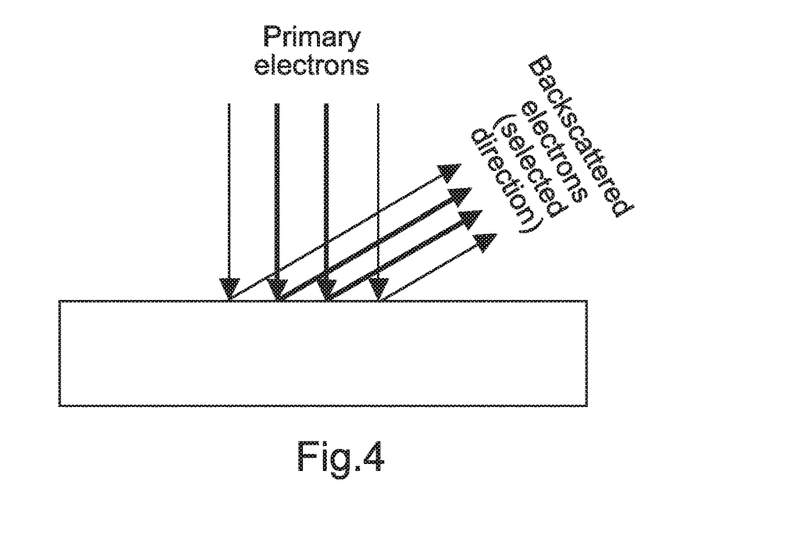
FIG. 4 shows an example of electrons emitted by a cathode interacting with an anode target resulting in the emission of backscattered electrons.

FIG. 4 shows electrons interacting with an anode surface, where back-scattered electrons (BSE) are emitted. X-rays are also emitted, however X-rays are generated at different depths within the anode leading to absorption and scattering of some X-rays which can be considered to be a filtering of the X-ray beam and reduction in X-ray flux. This situation is exacerbated as the anode surface becomes roughened, because X-rays that are generated near to the surface of the anode that previously would not have travelled through much of the anode and therefore not be particularly filtered, can now be generated within a trough of the anode surface and have to pass through an increased thickness of anode before finally exiting the anode surface, and as such the X-ray beam has increased filtering, leading to a drop in X-ray flux.

The Healthcare imaging industry is moving towards a new business model of leasing the imaging equipment or selling X-ray equipment with an indication that the uptime of the machine will be kept to the maximum. It is therefore desirable to monitor and maintain the performance of the tube continuously, without new investments in hardware (sensors) or major design changes or frequent visits from a field service engineer (FSE) to the field. Currently an X-ray tube needs frequent adaptation based on usage (for example twice a year) from both cathode and anode side. The cathode current adaptation is done to reset cathode current (to compensate change is resistance with time) to get the same emission current, and a separate tube yield calibration is done to check the output of the X-ray flux and image quality. As discussed in relation to FIG. 4, deterioration of the anode surface leads to a change in the X-ray flux. The apparatus for generating X-rays, system for imaging an object, and method for generating X-rays addresses this issue.

Figure 5:
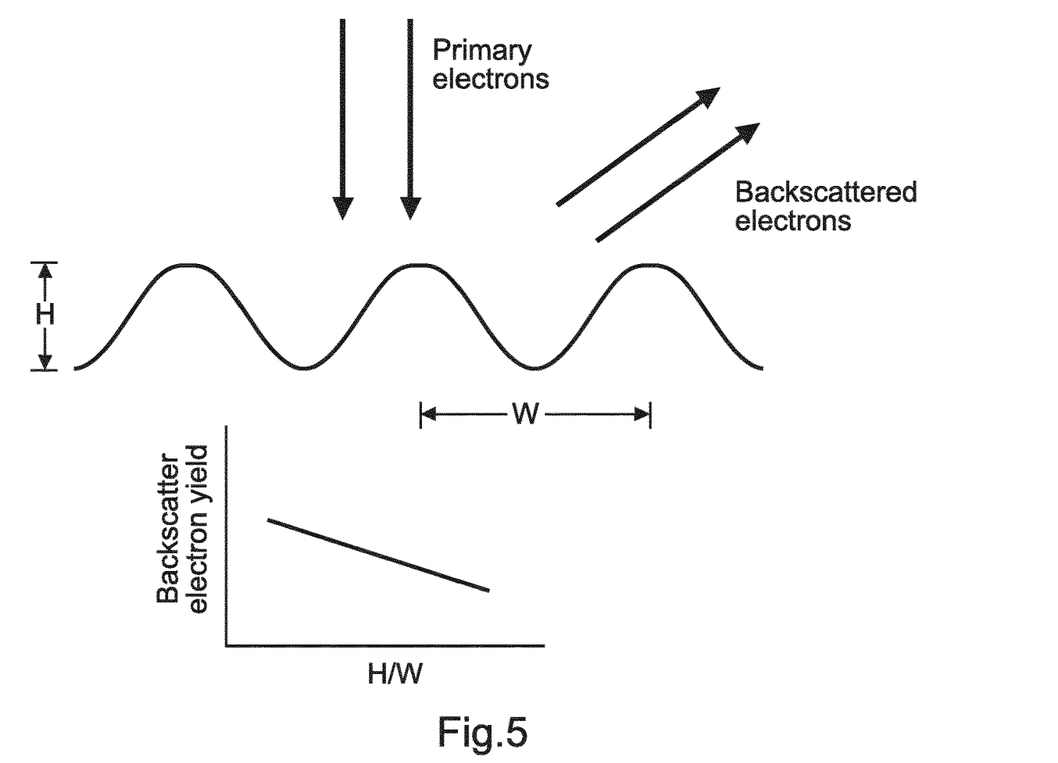
FIG. 5 shows an example of electrons emitted by a cathode interacting with an anode target having a surface roughness with an associated graph showing the yield of backscattered electrons as a function of the height to width ratio of surface features.
Figure 6:
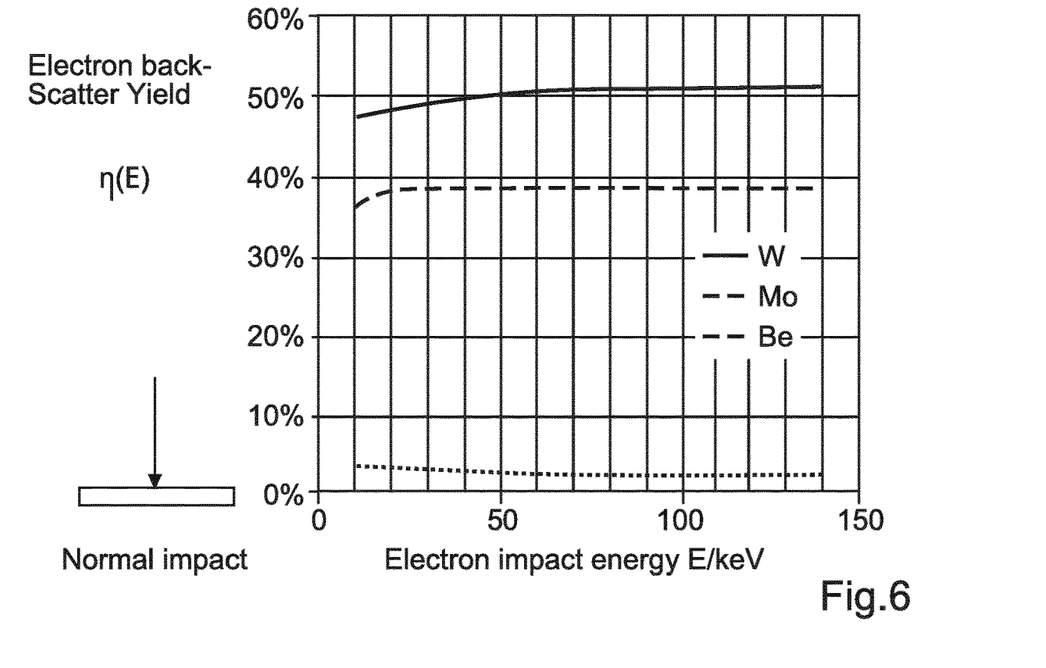
FIG. 6 shows the electron backscatter yield different elements as a function of electron impact energy.

FIG. 5 shows a situation similar to that shown in FIG. 4, except that the primary electrons, those electrons emitted by the cathode, interact with an anode that exhibits a surface roughness. The surface of the anode is represented as having surface features with a height H and a width W, and it has been shown that the yield of the backscattered electrons depends on a normalized surface roughness (H/W) represented in the graph of FIG. 5. In more detail, for roughness below 0.1, the backscatter electron yield is the same as for a flat surface and with an increase in roughness, the yield decreases continuously. At the focal spot where the electron beam strikes, the number of backscattered electrons detected gives direct information on the roughness and angle of the anode target; see for example Jpn. J. Appl. Phys. Vol. 33 (1994) pp. 4727-4734. As shown in FIG. 6 the electron backscatter yield (the yield of Backscattered electrons BSE) is independent of the impact energy, in other words acceleration voltage, and as such a measurement of backscattered electrons can be correlated with a measure of the roughness of the anode surface. As known correlations exist between anode surface roughness and the X-ray output spectra, as discussed in the background section, a backscattered electron current connected inside the X-ray tube can be correlated with the roughness of the anode, which in turn can be correlated to X-ray spectra. This enables the cathode current and/or X-ray tube voltage to be adjusted to maintain the X-ray flux at an appropriate level. In other words, a backscattered electron current is measured as an indicator for a degree of anode roughness, and this is used as a feedback to correct the cathode current and/or X-ray tube voltage.

Figure 7:
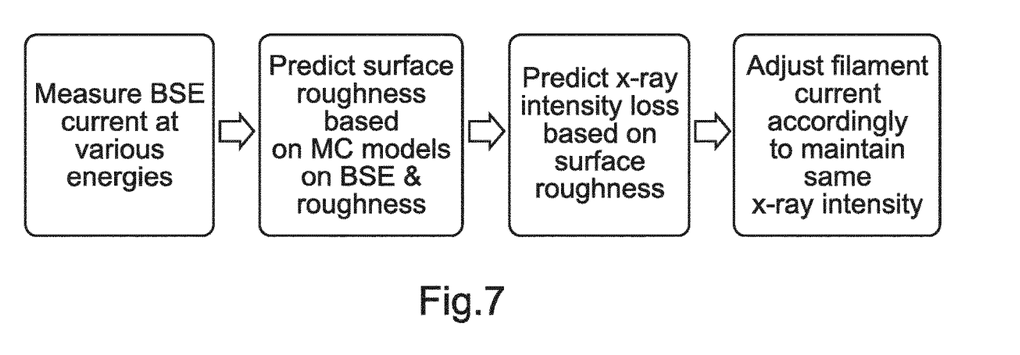
FIG. 7 shows a detailed workflow for generating X-rays.
Figure 8:
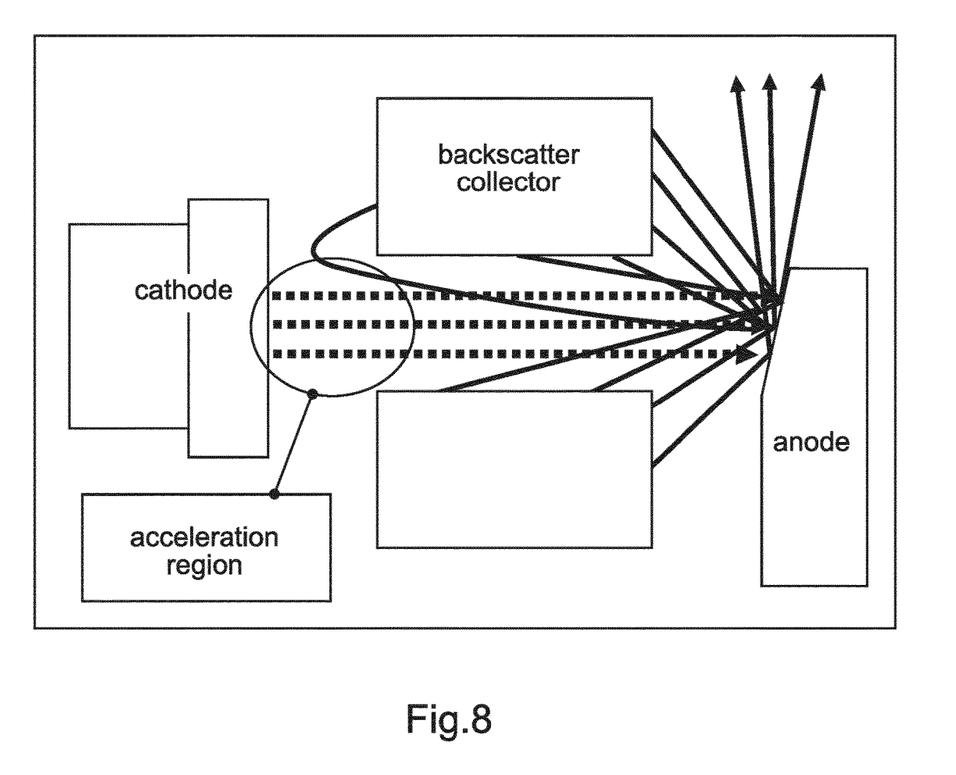
FIG. 8 shows a schematic set up of an example of an apparatus for generating X-rays.

FIG. 7 shows a detailed workflow for maintaining the same X-ray intensity or X-ray flux. For a particular system, and empirical calibration study is carried out to correlate different degrees of roughness with backscatter electron current and correlate different degrees of roughness with a loss of X-ray flux. The measured backscattered electron current is then used to provide a value for the loss of X-ray flux, and this is used to adjust the cathode current accordingly. The workflow shows the correction for cathode current, but can also apply for the correction to the X-ray tube voltage, where in addition to or alternatively the X-ray tube voltage can be adjusted to maintain the same intensity. As the backscattered electron yield is independent of acceleration voltage, the backscatter electron current can be measured without the X-ray tube operating at high KV or operating with full anode rotational speed. By measuring the backscattered electron current regularly, the X-ray flux from the X-ray tube can be maintained. Furthermore, as described with reference to FIG. 1 and above, and FIG. 9 below, a scintillator can be used with the backscatter electron detector to detector the X-ray flux from the anode. This can be used with the backscatter electron current to better adjust the cathode current and/or tube voltage. A schematic of the X-ray tube is shown in FIG. 8.

To address fluctuations in the location and size of the electron beam focal spot on the anode the apparatus provides for sensing the electron beam focal spot, enabling closed-loop control of the focal spot characteristics by a high voltage generator that is controlling the focusing and deflection fields thereby stabilizing the size and location of the electron beam focal spot.

Figure 9:
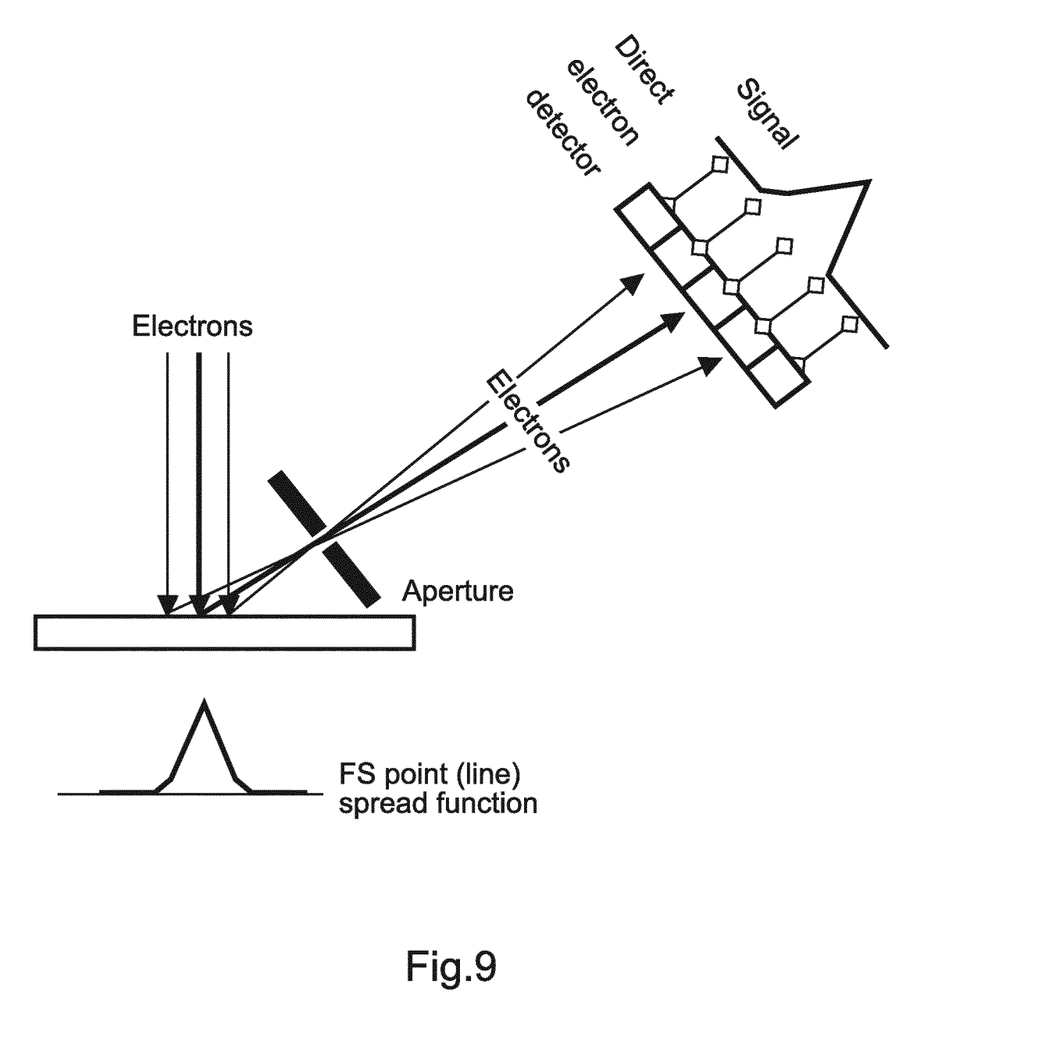
FIG. 9 shows a schematic set up of an example of a detector used to detect backscattered electrons.

FIG. 9 schematically shows how the apparatus achieves this. A pixeled detector that can directly detect electrons is positioned on the far side of a small diaphragm (e.g. a pinhole camera) to the focal spot. Direct electron detection has been established technology (DDD) for transmission microscopy electron imaging, see for example http://www-.directelectron.com/products/de-series where frame rates can reach 1000 frames per second. By directly detecting electrons, rather than converting electrons and photons of the scintillator and then detecting those photons, orders of magnitude larger electron flux can be measured compared to photon flux. This results in improved signal speed, spatial resolution (no scintillator) and dynamic range. When sent through a small enough diaphragm (e.g. a pinhole camera), the local electron flux behind maps the flux distribution in the focal spot (point spread function) if the electric field between FS and diaphragm is small enough to allow for a 1:1 mapping. E.g. in the Philips iMRC unipolar anode grounded tube backscattered electrons see a potential difference in the order of only a few % of the tube voltage. The electron flux distribution is detected downstream of the diaphragm in field-less space with spatially distributed electron capturing electrodes (direct detection). It is not necessary to convert the FS image into a photonic X-ray image. An "electronic image" suffices and will deliver a relatively high signal strength.

The rate of backscattered vs. primary electrons is hardly depending on the kinetic energy of the primaries, as discussed above. The flux of scattered electrons is therefore insensitive to the tube acceleration voltage. This simplifies achieving a high dynamic range. It is to be noted that whilst the photon flux is proportional to the square of the tube voltage, the electron flux is nearly constant. The scattered electron rate is insensitive to small deviations in the arrival angle of electrons at the anode, and as the focusing means of X-ray tubes cause only minor deviations (e.g.)+−20° in electron arrive in angles the scattered electron rate is insensitive to such small deviations. Therefore, the detected back-scattered electron flux truly maps the flux pattern of incoming electrons at the focal spot. Scattered electrons emerge in a wide range of directions. Their flux is significant even at 60° off the normal. The backscatter pinhole electron camera can therefore be placed outside the fan beam of used X-rays and still deliver a high signal.

Specific embodiments are:
Use of pixelated low electron scatter materials to capture the electrons (low-Z for example carbon, Be);

Use of a diaphragm of a low-Z (low backscatter material, coated or bulk);

Use of avalanche detectors (electron-multipliers);

Combination of photonic and electronic detection. Measuring electron flux and X-ray flux at the same time (thin electron capturing electrode on top of scintillator/photodiode pairs). Will allow to measure the tube voltage (ratio of electron to photon flux depends on the tube voltage) and the tube current (proportional to the total signal from backscattered electrons);

Combination of readout electronics for photodiodes with electron capturing electrodes (gain correction, bias);

Use of an electron transmitting foil (e.g. a diamond foil) to separate anode space and camera space (prevent contamination of the camera);

Electron detection behind such a foil in the open atmosphere or an inert gas atmosphere.

Thus, no frequent calibration and FSE visits are necessary to calibrate the X-ray tube yield as this can be monitored remotely. In addition, no additional sensors are required to monitor the X-ray tube degradation. Since the backscatter electron yield generation is independent of kV, such monitoring does not require high KV application or X-ray generation. This can help predict remaining lifetime of anode, correct the X-ray intensity loss due to roughness, increase the uptime of the system and save cost by reducing number of visits of a FSE. There is also the potential to combine both cathode adaptation and tube yield adaptation into one automated adaptation process for future systems of all imaging modalities.

In another exemplary embodiment, a computer program or computer program element is provided that is characterized by being configured to execute the method steps of the method according to one of the preceding embodiments, on an appropriate system.

The computer program element might therefore be stored on a computer unit, which might also be part of an embodiment. This computer unit may be configured to perform or induce performing of the steps of the method described above. Moreover, it may be configured to operate the components of the above described apparatus and/or system. The computing unit can be configured to operate automatically and/or to execute the orders of a user. A computer program may be loaded into a working memory of a data processor. The data processor may thus be equipped to carry out the method according to one of the preceding embodiments.

This exemplary embodiment of the invention covers both, a computer program that right from the beginning uses the invention and computer program that by means of an update turns an existing program into a program that uses invention.

Further on, the computer program element might be able to provide all necessary steps to fulfill the procedure of an exemplary embodiment of the method as described above.

According to a further exemplary embodiment of the present invention, a computer readable medium, such as a CD-ROM, USB stick or the like, is presented wherein the computer readable medium has a computer program element stored on it which computer program element is described by the preceding section.

A computer program may be stored and/or distributed on a suitable medium, such as an optical storage medium or a solid state medium supplied together with or as part of other hardware, but may also be distributed in other forms, such as via the internet or other wired or wireless telecommunication systems.

However, the computer program may also be presented over a network like the World Wide Web and can be downloaded into the working memory of a data processor from such a network. According to a further exemplary embodiment of the present invention, a medium for making a computer program element available for downloading is provided, which computer program element is arranged to perform a method according to one of the previously described embodiments of the invention.

It has to be noted that embodiments of the invention are described with reference to different subject matters. In particular, some embodiments are described with reference to method type claims whereas other embodiments are described with reference to the device type claims. However, a person skilled in the art will gather from the above and the following description that, unless otherwise notified, in addition to any combination of features belonging to one type of subject matter also any combination between features relating to different subject matters is considered to be disclosed with this application. However, all features can be combined providing synergetic effects that are more than the simple summation of the features.

While the invention has been illustrated and described in detail in the drawings and foregoing description, such illustration and description are to be considered illustrative or exemplary and not restrictive. The invention is not limited to the disclosed embodiments. Other variations to the disclosed embodiments can be understood and effected by those skilled in the art in practicing a claimed invention, from a study of the drawings, the disclosure, and the dependent claims.

In the claims, the word "comprising" does not exclude other elements or steps, and the indefinite article "a" or "an" does not exclude a plurality. A single processor or other unit may fulfill the functions of several items re-cited in the claims. The mere fact that certain measures are re-cited in mutually different dependent claims does not indicate that a combination of these measures cannot be used to advantage. Any reference signs in the claims should not be construed as limiting the scope.

The invention claimed is:

1. An apparatus for generating X-rays, comprising:
a cathode;
an anode;
at least one power supply;
an electron detector; and
a processor;
wherein the at least one power supply is configured to produce a voltage between the cathode and the anode;
wherein the at least one power supply is configured to provide the cathode with a cathode current;
wherein the cathode is positioned relative to the anode, and the cathode and the anode are operable such that electrons emitted from the cathode interact with the anode with energies corresponding to the voltage, and wherein the electrons interact with the anode at a focal spot to generate X-rays;
wherein the electron detector is positioned relative to the anode, and is configured to measure a backscatter electron signal from the anode;
wherein the electron detector is configured to provide the measured backscatter electron signal to the processor;
wherein the processor is configured to determine a correction to the cathode current and/or a correction to the voltage between the cathode and the anode by utilizing the measured backscatter electron signal and a correlation between an anode surface roughness and a backscatter electron emission; and wherein the processor is configured to provide the correction to the cathode current and/or the correction to the voltage between the cathode and the anode to the at least one power supply.

2. The apparatus according to claim 1, wherein the processor is configured to utilize a correlation between the anode surface roughness and an X-ray emission.

3. The apparatus according to claim 1, wherein the measured backscatter electron signal comprises a backscatter electron current.

4. The apparatus according to claim 1, wherein the electron detector comprises a plurality of electron detecting elements and an aperture, and wherein the aperture is positioned between the anode and the plurality of electron detecting elements.

5. The apparatus according to claim 4, wherein the processor is configured to determine a size of the focal spot by utilizing the measured backscatter electron signal.

6. The apparatus according to claim 5, wherein the at least one power supply is configured to provide at least one voltage to focus the electrons at the focal spot; and wherein the processor is configured to determine a correction to the at least one voltage to focus the electrons at the focal spot; and wherein the processor is configured to provide the correction to the at least one power supply.

7. The apparatus according to claim 4, wherein the processor is configured to determine a location of the focal spot by utilizing the measured backscatter electron signal.

8. The apparatus according to claim 1, wherein the measured backscatter electron signal comprises a backscatter electron flux.

9. The apparatus according to claim 1, wherein the electron detector is configured to measure an X-ray flux from the anode.

10. The apparatus according to claim 9, wherein the electron detector comprises a scintillator.

11. A system for imaging an object, comprising:
an apparatus for generating X-rays according to claim 1; and
an X-ray detector configured to acquire image data of an object.

12. A method for generating X-rays, comprising:
producing with at least one power supply a voltage between a cathode and an anode, wherein the cathode is positioned relative to the anode, and the cathode and the anode are operable such that electrons emitted from the cathode interact with the anode with energies corresponding to the voltage, and wherein the electrons interact with the anode at a focal spot to generate X-rays;
providing with the at least one power supply the cathode with a cathode current;
positioning an electron detector relative to the anode, and measuring a backscatter electron signal from the anode;
providing the measured backscatter electron signal to a processor;
determining with the processor a correction to the cathode current and/or a correction to the voltage between the cathode and the anode, wherein the determining comprises a utilization of the measured backscatter electron signal and a correlation between an anode surface roughness and a backscatter electron emission; and
providing the correction to the cathode current and/or the correction to the voltage between the cathode and the anode to the at least one power supply.

* * * * *